(12) United States Patent
Ure

(10) Patent No.: US 9,133,091 B2
(45) Date of Patent: Sep. 15, 2015

(54) PRODUCTION OF AROMATIC CARBOXYLIC ACIDS

(75) Inventor: Alan Macpherson Ure, Cleveland (GB)

(73) Assignee: INVISTA North America S.àr.l, Wilmington, DE (US)

( * ) Notice: Subject to any disclaimer, the term of this patent is extended or adjusted under 35 U.S.C. 154(b) by 0 days.

(21) Appl. No.: 13/698,540

(22) PCT Filed: May 4, 2011

(86) PCT No.: PCT/US2011/035196
§ 371 (c)(1),
(2), (4) Date: Jan. 28, 2013

(87) PCT Pub. No.: WO2011/146242
PCT Pub. Date: Nov. 24, 2011

(65) Prior Publication Data
US 2013/0267733 A1    Oct. 10, 2013

Related U.S. Application Data

(60) Provisional application No. 61/345,799, filed on May 18, 2010.

(51) Int. Cl.
*C07C 51/265* (2006.01)
*C07C 51/44* (2006.01)
*C07C 51/47* (2006.01)

(52) U.S. Cl.
CPC ............... *C07C 51/265* (2013.01); *C07C 51/44* (2013.01); *C07C 51/47* (2013.01)

(58) Field of Classification Search
CPC .................................................... C07C 51/265
See application file for complete search history.

(56) References Cited

U.S. PATENT DOCUMENTS

| 5,723,656 | A | 3/1998 | Abrams |
| 2004/0249208 | A1 | 12/2004 | Lin et al. |
| 2005/0038288 | A1 | 2/2005 | Lin et al. |
| 2005/0272951 | A1 | 12/2005 | Noe et al. |
| 2010/0249457 | A1 | 9/2010 | Jang et al. |

FOREIGN PATENT DOCUMENTS

| EP | 06355474 A1 | 1/1995 |
| EP | 0764627 A1 | 3/1997 |

OTHER PUBLICATIONS

Mooren, Nicolai, Supplementary European Search Report dated Oct. 29, 2013 for European Application No. 11783943.1, 6 pages.
International Preliminary Report on Patentability received for PCT Patent Application No. PCT/US2011/035196, mailed on Nov. 29, 2012, 6 pages.
International Search Report received for PCT Patent Application No. PCT/US2011/035196, mailed on Jan. 16, 2012, 5 pages.
Written Opinion received for PCT Patent Application No. PCT/US2011/035196, mailed on Jan. 16, 2012, 4 pages.

*Primary Examiner* — Yong Chu
*Assistant Examiner* — Ana Z Muresan
(74) *Attorney, Agent, or Firm* — William J. Simmons

(57) ABSTRACT

Disclosed are processes and systems for the production of aromatic carboxylic acids, such as purified terephthalic acid. The processes result in reduced volatile aromatic monocarboxylic acid contamination throughout various stages of the PTA process when compared to known processes. This permits the various effluent streams to be recycled back to several stages in the production process, which allows for the efficient production of pure PTA at a lower cost.

16 Claims, 1 Drawing Sheet

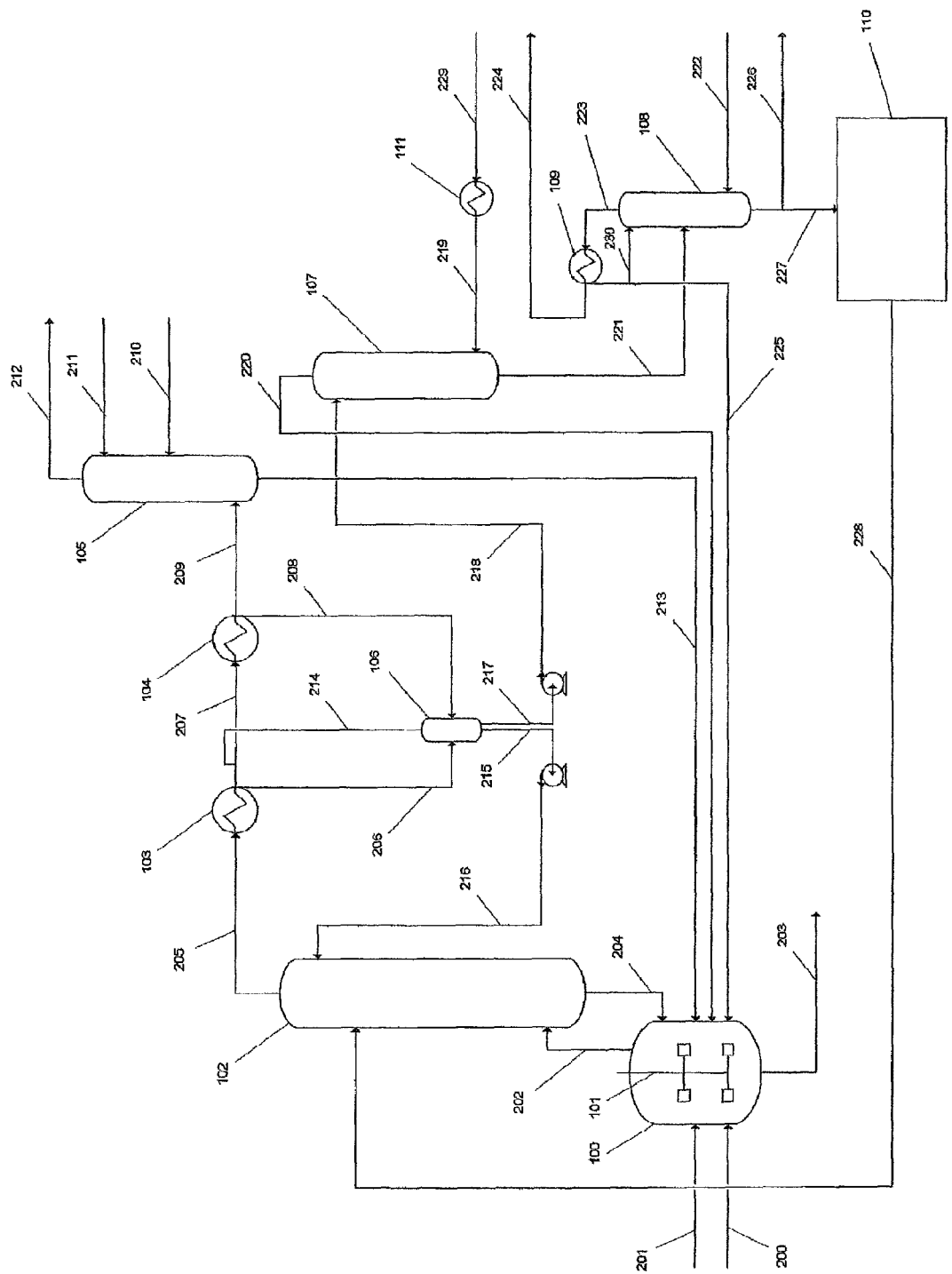

PRODUCTION OF AROMATIC CARBOXYLIC ACIDS

CROSS-REFERENCE TO RELATED APPLICATION

This application claims benefit of priority from U.S. Provisional Application No. 61/345,799 filed May 18, 2010.

FIELD OF THE INVENTION

This invention relates to processes and systems for the production of aromatic carboxylic acids, such as purified terephthalic acid (PTA). One aspect of the invention concerns a more efficient method of producing aromatic carboxylic acids. Another aspect concerns a method to reduce the amount of effluent generated by the production of aromatic carboxylic acids.

BACKGROUND OF THE INVENTION

Aromatic polycarboxylic acids, such as terephthalic acid, are important chemical intermediates used for the production of industrially significant products, including polyester polymers, which can be used for fiber production and in the manufacture of containers, bottles and other molded articles.

Purified terephthalic acid (PTA) can be produced in a two stage process. Current technology for the manufacture of terephthalic acid involves the liquid phase oxidation of an aromatic feedstock, such as paraxylene, using molecular oxygen in a solvent. The oxidation solvent comprises a lower (e.g. $C_2$-$C_6$) aliphatic carboxylic acid, usually acetic acid and water, in the presence of a dissolved heavy metal catalyst system usually incorporating a promoter, such as bromine. Acetic acid is particularly useful as the solvent since it is relatively resistant to oxidation and increases the activity of the catalytic pathway for the oxidation of aromatic feedstock and reaction intermediates. The reaction is carried out in one or more stirred vessels under elevated temperature and pressure, in the range of about 150 to 250° C. and 6 to 30 barA respectively and typically produces crude terephthalic acid (CTA) in high yield, e.g. at least 95%. Under these conditions the CTA precipitates from the solvent in the oxidation reactor to form a slurry of CTA solids in oxidation solvent, which is maintained in suspension by agitation in the reaction vessels. The temperature of the slurry is reduced by passing through a series of crystallizers, each at successively lower pressure, before the CTA solids are separated from the oxidation reaction solvent to give the oxidation mother liquor. The separation of the CTA solids from the oxidation mother liquor occurs at positive pressure or under vacuum.

Typically, the solvent for the liquid phase oxidation is aqueous acetic acid and contains water resulting from the oxidation of paraxylene and other reaction precursors. The oxidation reaction is exothermic and generates aromatic carboxylic acid, reaction intermediates from the partial oxidation of the aromatic feedstock and by-products, comprising colour-forming compounds, volatile components, such as methanol, methyl acetate and methyl bromide and degradation products such as carbon dioxide, carbon monoxide (carbon oxides) and benzoic acid (BA).

The second stage of the production process is the purification of CTA by catalytic hydrogenation in aqueous solution. Typically, CTA solids are dissolved in water at high pressure (70-90 barA) and high temperature (275-290° C.), and hydrogenated over a fixed bed catalyst of palladium supported on carbon. The resulting solution is cooled as it passes through a series of crystallizers, where the purified terephthalic acid (PTA) is crystallized. The resulting slurry at a temperature in the range of about 140-160° C. is fed to a suitable continuous solid liquid separation device(s), such as a centrifuge or rotary filter, where the PTA solids are separated from the purification mother liquor stream, washed and then dried.

The oxidation reaction is maintained at a constant temperature by evaporation of the oxidation solvent which exits the reactor and returning condensed solvent, which can also be further cooled, to the reactor. In this way, the latent heat of the oxidation solvent is used to cool the oxidation reaction mixture. The vapor phase leaving the reactor, as vent gas, typically comprises vaporized acetic acid, water vapour and volatile reaction by-products, as well as non-condensable components including residual oxygen not consumed in the oxidation reaction, nitrogen (when air is used as a source of the molecular oxygen for the oxidation reaction) and carbon oxides.

Typically, water in the oxidation solvent in the oxidation reactor is maintained at a constant level by condensing the off-gas from the oxidation reactor to form a condensate, separating the condensate from the remaining gas stream and separating at least a portion of the water from the rest of the liquid condensate, before returning the remaining liquid condensate to the reactor as oxidation solvent. The excess water separated from the condensate can be fed to an effluent treatment unit for disposal.

The separation of water from the oxidation reactor off-gas condensate can most easily be carried out by distillation, with the lower aliphatic monocarboxylic acid-rich stream as the bottoms product and a water-rich stream as the tops product. A previous improvement to the production process was to eliminate the initial condensation step and consisted of feeding the oxidation reactor off-gas directly to a rectifier column. This column can be conveniently located above the oxidation reactor for the lower aliphatic monocarboxylic acid-rich stream to return directly to the oxidation reactor, although other configurations can also be used.

The oxidation reactor operates at elevated pressure and temperature and the vent gas from the oxidation reactor can be used to recover energy down stream of the rectification column. Energy recovery can be either direct or indirect; by heat exchange, for example to raise steam for use elsewhere in the process or by reducing the pressure of the gas stream through a machine, such as an expander. The expander can be used to recover energy, e.g. to power the air compressor feeding air to the oxidation process or to generate electricity.

To purify terephthalic acid suitable for the manufacture of polyester polymer to manufacture fibers, bottles, containers and other molded products, crude terephthalic acid is dissolved in water at high temperature and pressure before being hydrogenated over a heterogeneous catalyst. The purification stage can be used to remove reaction intermediates and by-products that are known to cause or correlate with color-formation in polyester polymer. In particular, the reaction intermediate p-toluic acid (p-Tol), an aromatic monocarboxylic acid, is additionally formed by the hydrogenation of the oxidation reaction intermediate 4-carboxybenzaldehyde (4CBA), a contaminant in CTA that has to be reduced or eliminated to produce PTA. As p-Tol is substantially water-soluble under the conditions used for purification, it is largely retained in solution as PTA solid crystals in multiple vessels downstream of the hydrogenation reactor and in the purification mother liquor, following separation of the PTA solids from the crystallized PTA slurry. Some p-Tol co-crystallizes with PTA, the amount being dependent on the process conditions. The p-Tol in solution is a yield loss for the conversion of paraxylene to PTA and restricts the use of the purification mother liquor as a source of water for use elsewhere in the production process.

To separate the lower aliphatic carboxylic acid from water recovered as condensate from the oxidation reactor off-gas, an adequate number of separation stages in the rectification column and sufficient aqueous reflux to the top of the column are required. However, the total flow of aqueous reflux back to the top of the column is constrained by maintaining the oxidation reactor water concentration at a target value. Typically, the aqueous reflux comprises a portion of the overheads product after condensing the water-rich vapor stream leaving the top of the rectifier column. The rest of the rectification column condensate, typically mostly water of reaction, is then removed from the rectifier overheads system.

An existing and alternative process is to remove a substantial portion of the overheads water condensate for use as make-up water on the purification stage of the PTA manufacturing process, with reflux to the rectifier being provided by a combination of pure plant mother liquor and a smaller portion of rectifier overheads condensate. The pure plant mother liquor contains significant concentrations of p-Tol, BA and other reaction intermediates and by-products, so this stream is returned to the rectifier several stages below the top of the column. The cleaner rectifier overheads condensate is returned to the top of the rectifier and removes volatile impurities from the pure plant mother liquor reflux from the rectifier overheads vapor stream, allowing the subsequent overheads condensate to be re-used elsewhere in the process. However, if the rectifier overheads condensate is used to supply the majority of the process water needs and if most or all of the pure plant mother liquor is returned as reflux to the rectifier, the amount of water reflux provided by rectifier overheads condensate is too low to remove the volatile components from the pure plant mother liquor and maintain the required purity of the rectifier overheads condensate without a disproportionate number of stages being required in the top scrubbing section of the rectifier. In particular, the concentrations of p-Tol and BA in the rectifier overheads condensate would make it unsuitable for use as make-up water on the purification stage of the PTA manufacturing process, where water substantially free of these components is required.

The consequence of these combined problems reduces the economic benefit of using a rectification column to separate water from the oxidation solvent, which would otherwise enable water recycle between the oxidation and purification stages of the PTA manufacturing process and simplify recovery of oxidation reaction intermediates from the purification process.

SUMMARY OF THE INVENTION

Therefore, a need exists to improve the method of operation of a rectifier as a distillation device. Specifically, there is a need to beneficially separate water and process solvent from the oxidation reactor vent gas, to allow water recycle between the oxidation and purification stages, and to enable recovery of oxidation reaction intermediates from the purification stage of the PTA manufacturing process.

In one aspect, a method for producing aromatic polycarboxylic acid is disclosed comprising: a) separating an oxidation reactor vent gas stream into an acetic acid rich stream and a water rich vapor stream, wherein the water rich vapor stream comprises volatile compounds and non-condensable gases, and said separating is performed in a distillation device; b) condensing said water rich vapor stream into a condensate stream and a vapor stream; c) feeding a first portion of said condensate stream to said distillation device and feeding a second portion of said condensate stream to an extraction column; and d) removing organic compounds from said second portion of said condensate to form an organic product stream and a aqueous product stream. The distillation device can be a rectifier.

Also, at least part of the distillation device overheads condensate can be fed to a liquid-liquid extraction system to selectively remove the organic components from the condensate into an organic liquid phase, leaving an aqueous phase with low levels of contaminants, suitable for re-use elsewhere in the production process. Here, the separation duty of the distillation device does not need to be increased and the purification stage can be integrated with the oxidation stage of the PTA manufacturing process. The quantity of water fed to an effluent treatment unit can also be reduced. Further, the oxidation reaction intermediates from the pure plant mother liquor can be recovered and recycled to the oxidation reactor. This increases the efficiency and conversion of the feedstock to aromatic carboxylic acid products. Optionally, the volatile organic components in the oxidation reactor off-gas can be recovered and recycled to the oxidation reactor.

In another aspect, a method for producing terephthalic acid is disclosed comprising: a) adding paraxylene, molecular oxygen, and acetic acid to an agitated oxidation reactor; b) removing reactor vent gas from said oxidation reactor, wherein said reactor vent gas comprises acetic acid and water vapor; c) feeding said reactor vent gas to a distillation column, wherein the reactor vent gas is separated into an acetic acid rich stream that is fed back to said oxidation reactor and into a water vapour rich stream that is fed to a condenser; d) condensing said water vapour rich stream into a condensate stream and a vapor stream, wherein a first portion of said condensate stream is fed back to said distillation column and a second portion of said condensate stream is fed to an extraction column; e) feeding said vapor stream to an absorber to remove volatile components retained in the vapor; f) feeding to said extraction column paraxylene in a countercurrent direction to said second portion of said condensate stream; g) extracting organic compounds from said second portion of said condensate stream to form an aqueous stream, and feeding the organic compounds to said oxidation reactor; h) feeding said aqueous stream to a water treatment column to remove volatile components, wherein the volatile components are recovered as vapor and condensed to form reflux; i) feeding a first portion of said reflux back into said water treatment column and feeding a second portion of said reflux back into said oxidation reactor; and j) feeding steam to the base of the water treatment column to remove remaining volatile components resulting in a fresh water stream substantially free of contaminants. The distillation column can be a rectifier.

BRIEF DESCRIPTION OF THE DRAWINGS

FIG. 1 is a schematic process diagram of one aspect of the disclosed process, which illustrates a continuous oxidation process showing the configuration of the rectifier and the extraction column.

DETAILED DESCRIPTION

Unless defined otherwise, all technical and scientific terms used herein have the same meaning as commonly understood by one of ordinary skill in the art to which this disclosure belongs. Any methods and materials similar or equivalent to those described herein can also be used in the practice or testing of the present disclosure.

In one aspect, an improved method is disclosed that increases the recovery of clean water for use in the manufacturing process by recycling water from the rest of the PTA manufacturing process and using it as liquid reflux at the top of the rectifier.

The production of aromatic carboxylic acids, including terephthalic acid, can take place in an agitated oxidation reactor. Here, an aromatic feedstock, e.g. paraxylene, is reacted with molecular oxygen, typically derived from air, reaction catalyst, and aqueous acetic acid solvent, to produce the carboxylic acid. The reaction temperature can be between about 150° C. to about 250° C., including 190° C.; and the pressure can be between about 6 bar absolute (barA) to about 30 barA, including 13 barA. CTA solids are precipitated in the reactor, as the product of the oxidation reaction is maintained in suspension by an agitator. Other feed streams to the oxidation reactor can comprise reflux solvent, recycled solvent, recovered paraxylene and recovered methyl acetate.

The slurry of CTA in the oxidation solvent (mother liquor) flows to crystallizers downstream of the oxidation reactor. The CTA solids are then separated from the oxidation mother liquor using a rotary filter, a centrifuge, or other similar device. The separation temperature ranges from about 90° C. to about 160° C., and the pressure from about 0.6 barA to about 4.5 barA. Also, the oxidation reaction intermediates can be recovered from the pure plant mother liquor and recycled to the oxidation reactor. This increases the efficiency and conversion of feedstock to aromatic carboxylic acid products.

The oxidation reaction is exothermic and the heat of reaction is removed by evaporation of solvent into the reactor vent gas that flows to a rectifier, which can be one or more vessels. Acetic acid and water in the reactor vent gas are separated by distillation, which operates with the distillation column overheads temperature in the range from about 140° C.-200° C., including about 170° C. The distillation can take place in a rectifier.

Aqueous reflux is supplied to the top of the distillation column from the overheads condensers, which can comprise one or more heat exchangers. Additional aqueous reflux comprising pure plant mother liquor, can be fed below the top of the column. An acetic acid rich stream from the base of the column can be returned to the oxidation reactor. The base of the column operates at about the same temperature as the oxidation reactor.

The water-rich vapor from the top of the column comprises acetic acid, typically 0.1 to 5% w/w, which is condensed and cooled down in stages to a temperature in the range from about ambient to about 100° C., including about 40° C. A portion of the condensate, typically at a temperature in the range from about 130° C. to about 160° C., is fed to the top of the column as aqueous reflux. The overheads condensers can comprise two or more heat exchangers, typically with at least one used to generate steam for efficient heat recovery from the column overheads. Uncondensed gas passes to an absorber at about 6 to about 30 barA to remove volatile components, such as paraxylene, methanol, methyl acetate and benzoic acid retained in the vapor.

The volatile components can be removed by contacting with liquid, first with an acetic acid rich stream, such as the oxidation solvent, and then with a water rich stream. The scrubbing liquors are fed to the oxidation reactor. Scrubbed vent gas from the top of the absorber comprising inert gas in the range from about 4 to about 28 barA, including about 11 barA, can be processed further, including energy recovery, for example by passing through an expander, before being vented to the atmosphere.

Further, at least part of the column overheads condensate can be fed to a liquid-liquid extraction system to selectively remove the organic components from the condensate into an organic liquid phase, leaving an aqueous phase with low levels of contaminants, suitable for re-use elsewhere in the production process. Here, a portion of the condensate from the column overheads is fed to the top of an extraction column to which fresh paraxylene can be fed to the bottom. Paraxylene as the organic phase extractant flows up the column countercurrent to the flow of condensate as the aqueous phase, which flows down the liquid-full column. The aqueous and organic phases are immiscible. The temperature of the organic and aqueous phases can be controlled, and the paraxylene stream can be preheated. Organic compounds comprising p-toluic acid, benzoic acid, methyl acetate, acetic acid and methanol, dissolved in the aqueous phase, are extracted into the organic phase, thereby substantially removing minor components and organic contaminants from the aqueous stream. The organic product from the top of the extraction column can be fed to the oxidation reactor as the main source of paraxylene feedstock.

To recover the volatile organic components, the bottom aqueous product from the extraction column flashes as it enters the water treatment column, which operates close to atmospheric pressure. Volatile components comprising paraxylene, methyl acetate and methanol are substantially separated from the aqueous stream and can be returned to the oxidation reactor. To enhance separation of the volatile components from the aqueous phase in the water treatment column, steam can be fed to the bottom of the column. Water from the base of the water treatment column is substantially free of contaminants and can be used elsewhere in the production process, for example, in the purification plant.

FIG. 1 describes one aspect of the disclosed process. Here, paraxylene is oxidized to CTA using molecular oxygen in an agitated reactor comprising one or more stirred vessels under elevated temperature and pressure. Specifically, the oxidation reactor 100 can be fed with air 200, aqueous acetic acid solvent 201, containing the reaction catalyst, and paraxylene 220. CTA solids are precipitated in the reactor, as the product of the oxidation reaction, and are maintained in suspension by an agitator 101. Other feed streams to the oxidation reactor can include reflux solvent 204 from rectifier 102; recycle solvent 213 from absorber 105; and recovered paraxylene, methyl acetate and methanol 225 from the water treatment column 108. The oxidation reaction is exothermic and the heat of reaction is removed by evaporation of solvent into the reactor vent gas 202. The reactor product 203, a slurry of CTA in the oxidation solvent, flows to more than one crystalliser in series downstream of the oxidation reactor, before the CTA solids are separated from the oxidation mother liquor using a suitable device.

The reactor off-gas 202 from the oxidation reactor 100 flows to a rectifier 102. Acetic acid and water in the reactor off-gas are separated by distillation in the rectifier. Aqueous reflux is supplied to the top of the rectifier via stream 216, which is a portion of the condensate produced in the overheads condensers 103 and 104, comprising one or more heat exchangers. Additional aqueous reflux 228 can be fed below the top of the rectifier, comprising pure plant mother liquor, resulting from the separation of PTA solids following crystallization in the purification stage. An acetic acid rich stream 204, from the base of the rectifier can be returned to the oxidation reactor.

The water-rich vapor 205, containing low levels of acetic acid, flows from the top of the rectifier to the rectifier overheads condensers 103 and 104. The condensers 103 and 104 comprise two or more heat exchangers with at least one used to generate steam for efficient heat recovery. The vapor 205 from the top of the rectifier is condensed and cooled down in stages. The condensate 206 and 208 can be separated from the vapor stream at each stage of condensation and flowed to a reflux pot 106, which can be pressure balanced, for example, via line 214 to the overheads vapor line 207. A portion of the condensate collected in reflux pot 106 flows to the top of the rectifier as aqueous reflux 215 and 216. Uncondensed gas 209 from the final heat exchanger passes to an absorber 105 to remove volatile components retained in the vapor. The volatile components are removed by contacting with liquids, including, first with an acetic acid rich stream, such as the oxidation solvent 210, and then with a water-rich stream 211. The scrubbing liquors 213, comprising acetic acid and water from the bottom of the absorber, flow to the oxidation reactor 100. Scrubbed vent gas 212 from the top of the absorber passes forward for further processing, including energy recovery, before being vented to the atmosphere.

Condensate 217 and 218 collected in the reflux pot 106 can also flow to the top of an extraction column 107 to which fresh paraxylene 219 can be fed to the bottom. Paraxylene 219 can be heated in exchanger 111, to facilitate operation of the extraction column 107. Paraxylene as the organic phase extractant flows up the column countercurrent to the flow of condensate as the aqueous phase, which flows down the liquid-full column. The aqueous and organic phases are immiscible. Organic compounds dissolved in the aqueous phase are extracted into the organic phase, thereby substantially removing minor components and organic contaminants from the aqueous stream. The organic product 220 from the top of the extraction column can flow to the oxidation reactor 100, as the main source of paraxylene feedstock to the reactor.

The bottom aqueous product 221 from the extraction column 107 flows to the water treatment column 108, where volatile components are separated from the aqueous product and recovered in the top vapor 223 which flows to condenser 109 where it is substantially condensed. A portion of the condensate from the water treatment column overheads condenser 109 is returned as reflux 230 to the column, while the rest 225 can be returned to the oxidation reactor 100. Non-condensable vapors 224 from the water treatment column overheads condenser 109 can be vented from the system.

To ensure separation of the volatile components from the aqueous phase, steam 222 can be fed to the bottom of the water treatment column 108. Water from the base of the water treatment column is substantially free of contaminants and can be used as fresh water make-up 227 elsewhere in the production process and especially in the purification plant 110. Excess water 226 can be sent to effluent treatment before or after any further treatment.

EXAMPLES

The following examples further illustrate the present invention.

A combination of physical measurements and modeling gives the results in the examples.

Example 1

A rectifier is configured, as shown in FIG. 1, to receive the vent gas from a CTA oxidation reactor and reflux an acetic acid-rich stream back to the reactor. The overheads from the rectifier are substantially condensed and a portion of the condensate is returned to the top of the rectifier as liquid reflux and the remainder is fed to the extraction column. The organic phase from the extraction column (stream 220) comprises paraxylene and is fed as feedstock to the CTA oxidation reactor. The aqueous phase from the extraction column is fed to the water treatment column, where volatile components are separated from the aqueous product to generate water that is substantially free of contaminants and can be used as fresh water make-up (stream 227) elsewhere in the production process and especially on the purification plant.

Table 1 shows the concentrations of aromatic monocarboxylic acids (i.e. contaminants) at key locations in the PTA production process. The recycled water must have very low contamination to act as a water wash for the PTA. Aromatic monocarboxylic acids, comprising benzoic and p-toluic acid are contaminants that are routinely monitored in the production process and must not exceed the target specification of the final PTA product.

Comparative Example 1

A system is configured as for Example 1, but without an extraction step to remove organic components from a portion of the rectifier overheads condensate, prior to the water treatment column.

Table 1 shows the increased level of aromatic monocarboxylic acids at key locations in the PTA production process in comparison to Example 1. The aqueous stream from the bottom of the water treatment column contains significant levels of organic components, such as aromatic monocarboxylic acids and can no longer be used in place of clean water elsewhere in the PTA manufacturing process. For example, PTA solids washed with the aqueous stream from the bottom of the water treatment column after separation from the purification plant mother liquor would be outside the product specification for contaminants comprising aromatic monocarboxylic acids.

Example 2

A system is configured as for Example 1, but the rectifier has a lower separation capacity by reducing the number of theoretical stages.

As shown in Table 1, the various aspects of the disclosed process result in reduced volatile aromatic monocarboxylic acid contamination throughout various stages of the PTA process when compared to known processes. The disclosed processes allow for the efficient production of PTA at a lower cost.

TABLE 1

Comparison of examples

| | Example 1 | Comparative example 1 | Example 2 |
|---|---|---|---|
| Volatile aromatic monocarboxylic acids extracted into organic phase (stream 220) % $^w/_w$ | 0.17 | — | 0.17 |
| Volatile aromatic monocarboxylic acids in water (stream 227) % $^w/_w$ | 0.008 | 0.073 | 0.008 |
| Theoretical stages in rectifier | 52 | 52 | 46 |
| Contribution to COD of volatile aromatic monocarboxylic acids % $^w/_w$ | 0.17 | 1.28 | 0.17 |
| PTA in specification using recovered water as make-up water in purification plant | Yes | No | Yes |

While the invention has been described in conjunction with specific embodiments thereof, it is evident that many alternatives, modifications and variations will be apparent to those skilled in the art in light of the foregoing description. Accordingly, the invention is intended to embrace all such alternatives, modifications and variations as fall within the spirit and scope of the claims.

What is claimed is:

1. An aromatic polycarboxylic acid manufacturing process comprising:
   a) separating an oxidation reactor vent gas stream into an acetic acid rich stream and a water rich vapor stream, wherein the water rich vapor stream comprises volatile compounds and non-condensable gases, and said separating is performed in a distillation device;
   b) condensing said water rich vapor stream into a condensate stream and a vapor stream;
   c) feeding a first portion of said condensate stream to said distillation device and feeding a second portion of said condensate stream to an extraction column; and
   d) removing at least one aromatic monocarboxylic acid from said second portion of said condensate to form an aromatic monocarboxylic acid stream and a aqueous product stream.

2. The process of claim 1 wherein said distillation device is a rectifier.

3. The process of claim 1 or 2 further comprising e) feeding the aromatic monocarboxylic acid stream to said oxidation reactor.

4. The process of claim 1 or 2 further comprising feeding the acetic acid rich stream to the oxidation reactor.

5. The process of claim 1 or 2 wherein a liquid extractant is used to remove the at least one aromatic monocarboxylic acid from said second portion of said condensate.

6. The process of claim 5 wherein the liquid extractant is an aromatic feedstock oxidized in the oxidation reactor.

7. The process of claim 5 further comprising e) separating volatile products from said aqueous stream to generate a water stream that is substantially free of contaminants.

8. The process of claim 7 wherein the resultant water stream is used as clean water in the manufacture of aromatic carboxylic acids.

9. The process of claim 8, wherein said aromatic carboxylic acid is terephthalic acid.

10. The process of claim 9 wherein the liquid extractant is paraxylene.

11. The process of claim 1 wherein said at least one aromatic monocarboxylic acid is selected from the group consisting of benzoic acid, p-toluic acid, and m-toluic acid.

12. The process of claim 5 wherein the height of the distillation device or rectifier is reduced by decreasing the number of separation stages and reducing the separation duty of the device or rectifier.

13. The process of claim 1 further comprising separating the oxidation reactor vent gas stream into a residual vent gas stream, wherein energy is recovered from the residual vent gas stream.

14. The process of claim 13, wherein said energy recovery is by a mechanical device.

15. The process of claim 14, wherein said mechanical device is an expander.

16. The process of one of claims 13-15, wherein the recovered energy can be used to generate electricity.

* * * * *